United States Patent [19]

Lin

[11] Patent Number: 5,603,455
[45] Date of Patent: Feb. 18, 1997

[54] DEODORIZER CONTAINER

[76] Inventor: Shi Huang Lin, P.O. Box 82-144, Taipei, Taiwan

[21] Appl. No.: 547,130

[22] Filed: Oct. 24, 1995

[51] Int. Cl.⁶ .................................................. A24F 25/00
[52] U.S. Cl. .................. 239/44; 239/47; 239/57; 239/326; 261/DIG. 17
[58] Field of Search ................ 239/34, 44, 47, 239/57, 58, 59, 145, 302, 326; 261/DIG. 17

[56] References Cited

U.S. PATENT DOCUMENTS

| | | | |
|---|---|---|---|
| 3,330,481 | 7/1967 | Dearling | 239/47 |
| 4,084,732 | 4/1978 | Dearling | 239/326 |
| 4,341,348 | 7/1982 | Dearling | 239/34 |
| 4,346,059 | 8/1982 | Spector | 239/57 |
| 4,759,501 | 7/1988 | Silvenis et al. | 239/326 |

*Primary Examiner*—Andres Kashnikow
*Assistant Examiner*—Lisa Ann Douglas
*Attorney, Agent, or Firm*—Alfred Lei

[57] ABSTRACT

A deodorizer container including a casing, an inner container fitted into the casing and designed for receiving liquid deodorizer, the inner container being provided with a spray nozzle at a top thereof, and an evaporation controller including an outer tube and an inner tube rotatably fitted into the outer tube, the outer tube being formed with a plurality of perforations, the outer tube being provided at an end with a cylindrical portion communicated with the outer tube through a slot, the cylindrical portion being adapted to receive the spray nozzle of the inner container, whereby the evaporation rate of the liquid deodorizer in the deodorizer container can be controlled as desired.

6 Claims, 4 Drawing Sheets

DEODORIZER CONTAINER

BACKGROUND OF THE INVENTION

1. Field of the Invention

This invention relates to an improved deodorizer container.

2. Description of the Prior Art

The conventional deodorizer container is simply a case with perforations. Hence, once the case is open for use, it will be impossible to control the evaporation rate of the deodorizer thereby causing extravagance. Furthermore, the conventional deodorizer container is often hung or fixedly adhered on an article, and cannot be conveniently mounted on the louver of an air-conditioner.

Therefore, it is an object of the present invention to provide a deodorizer container which can obviate and mitigate the above-mentioned drawbacks.

SUMMARY OF THE INVENTION

This invention relates to an improved deodorizer container.

It is the primary object of the present invention to provide a deodorizer container which is adjustable in evaporating rate as desired.

It is another object of the present invention to provide a deodorizer container which can prevent deodorizer from overspending.

It is another object of the present invention to provide a deodorizer container which can be easily mounted on an air-conditioner.

It is still another object of the present invention to provide a deodorizer container which is facile to manufacture and assemble.

It is a further object of the present invention to provide a deodorizer container which is fit for practical use.

Other objects of the invention will in part be obvious and in part hereinafter pointed out.

The invention accordingly consists of features of constructions and method, combination of elements, arrangement of parts and steps of the method which will be exemplified in the constructions and method hereinafter disclosed, the scope of the application of which will be indicated in the claims following.

DETAILED DESCRIPTION OF THE PREFERRED EMBODIMENT

Figure 1:
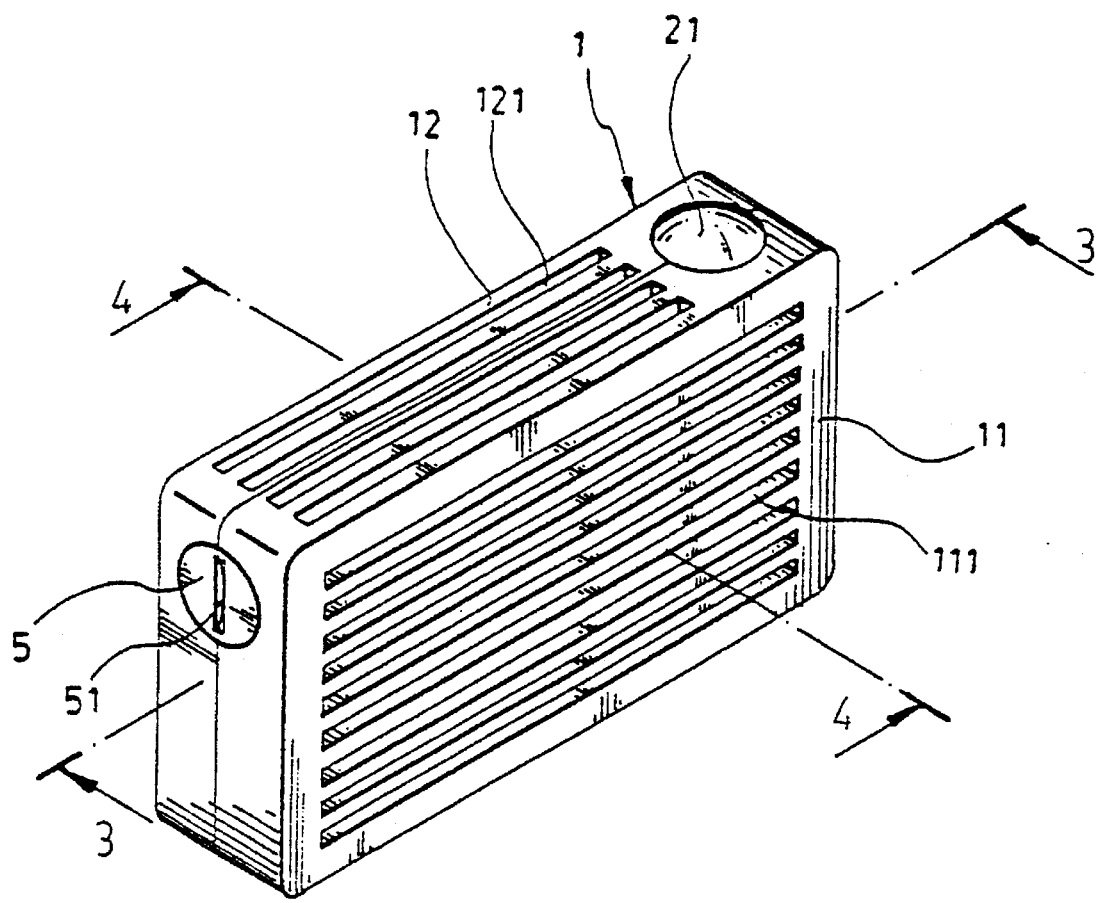
FIG. 1 is a perspective view of the present invention.

For the purpose to promoting an understanding of the principles of the invention, reference will now be made to the embodiment illustrated in the drawings. Specific language will be used to describe the same. It will, nevertheless, be understood that no limitation of the scope of the invention is thereby intended, such alternations and further modifications in the illustrated device, and such further applications of the principles of the invention as illustrated herein being contemplated as would normally occur to one skilled in the art to which the invention relates.

Figure 2:
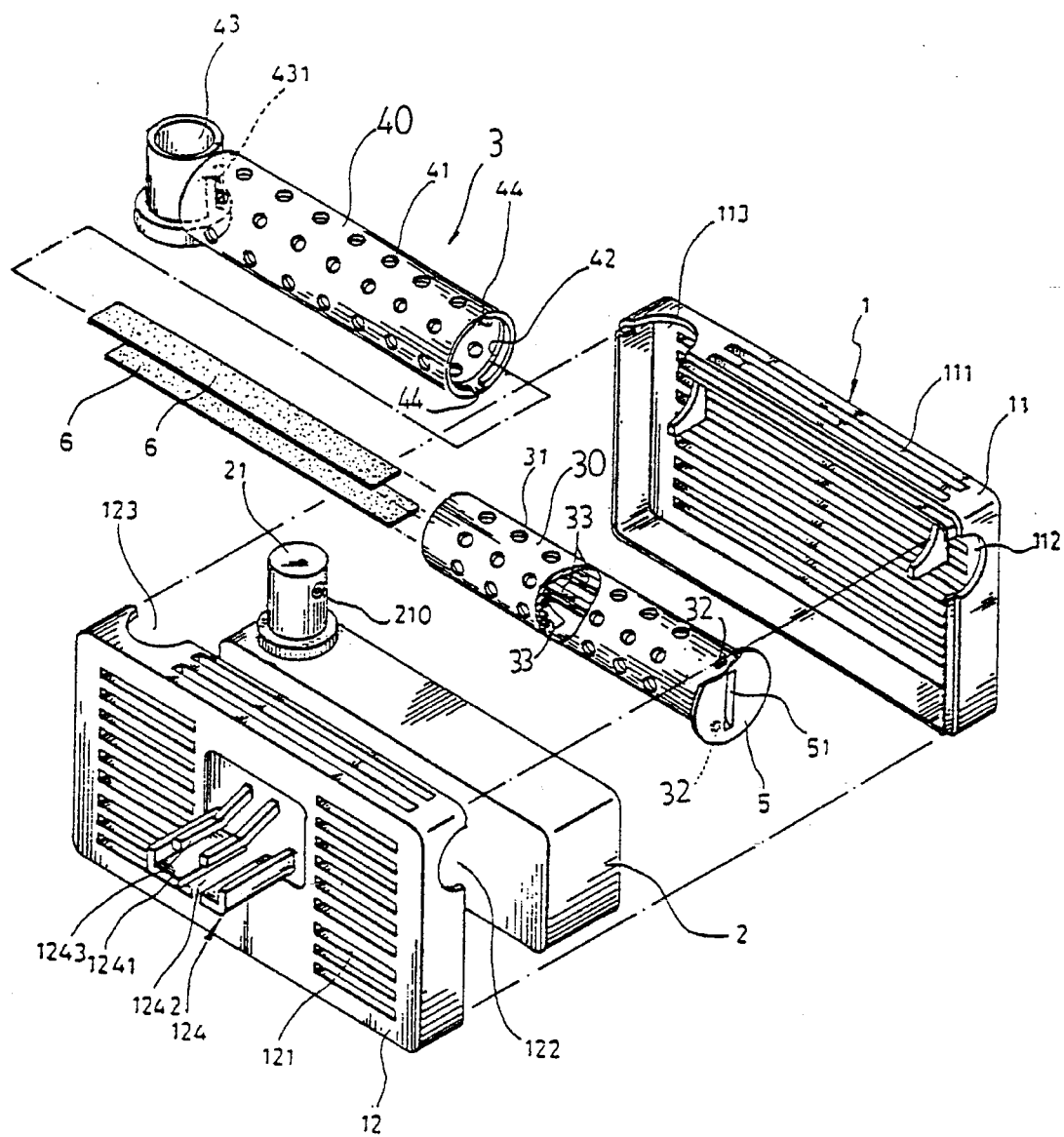
FIG. 2 is an exploded view of the present invention.
Figure 3:
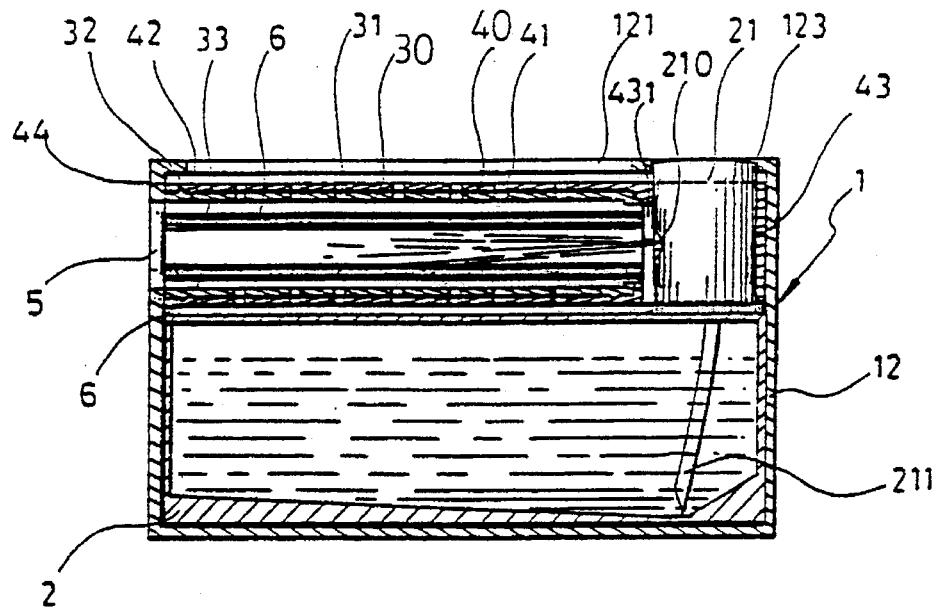
FIG. 3 is a sectional view taken along line 3—3 of FIG. 1.

With reference to the drawings and in particular to FIGS. 1, 2 and 3 thereof, the deodorizer container according to the present invention mainly comprises a casing 1, an inner container 2, and an evaporation controller 3.

The casing 1 is composed of a front rectangular cover 11 and a rear rectangular cover 12. The front rectangular cover 11 is formed with a plurality of first slots 111 at its front side, a first semi-circular recess 112 at its one end, and a second semi-circular recess 113 at its top. The rear rectangular cover 12 is also formed with a plurality of second slots 121 at its front side, a third semi-circular recess 122 at its one end adapted to engage with the first semi-circular recess 112 of the front rectangular cover 11 to form a circular opening, and a fourth semi-circular recess 123 at its top adapted to engage with the second semi-circular recess of the front rectangular cover 11 to form a circular opening. The outer side of the rear rectangular cover 12 is provided with a holder 124 which includes a pair of laterally symmetric L-shaped supporting members 1241 and a pair of positioning rod members 1243. The gap 1242 between the lower ends of the L-shaped supporting members has the same size as that between the lower ends of the positioning rod members 1243.

The inner container 2 for receiving liquid deodorizer is fitted between the front and rear rectangular covers 11 and 12. The inner container 2 is provided with a spray nozzle 21 having an output orifice 210. In addition, the inner container 2 has a sloping inner bottom so that all liquid deodorizer can be discharged through the spray nozzle 21.

Figure 4:
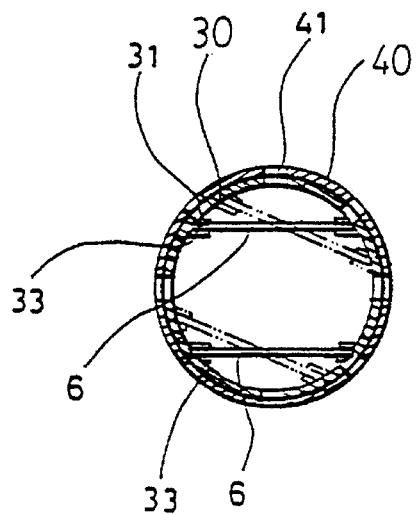
FIG. 4 is a sectional view of the evaporation controller taken along line 4—4 of FIG. 1.

The evaporation controller 3 is arranged within the casing 1 and located above the inner container 2. The evaporation controller 3 is composed of an inner tube 30 and an outer tube 40. The inner tube 30 is open at one end and has a plurality of perforations 31 thereon. The inner tube 30 is provided with a circular plate 5 at the other end on which there is an elongated groove 51. Further, the inner tube 30 has two opposite protuberances 32 close to the circular plate 5 and two pairs of oppositely aligned racks 33 at its interior surface. Two sheets of absorbent paper 6 are each inserted between a pair of oppositely aligned racks 33 (see FIG. 4). The outer tube 40 is also open at its one end and formed with a plurality of perforations 41 which are aligned with the perforations 31 of the inner tube 30. At the other end of the outer tube 40 there is a cylindrical portion 43 adapted to receive the spray nozzle 21. The cylindrical portion 43 has a vertical slot 431 thereby communicating the cylindrical portion 43 with the outer tube 40. The open end of the outer tube 40 is formed with a circular groove 42 and two opposite longitudinal notches 44 which extend from the outermost edge inwardly to the circular groove 44, so that the inner tube 30 may be inserted into the outer tube 40 with its protuberances 32 going into the circular groove 44 through the notches 44 and can be rotated with respect to the outer tube 40.

Figure 5:
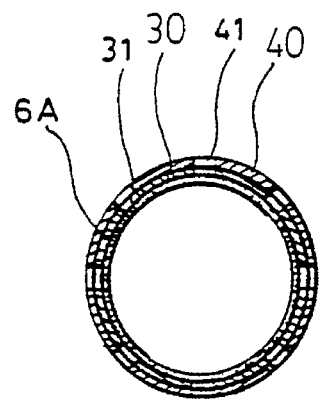
FIG. 5 is a sectional view illustrating a second preferred embodiment of the evaporation controller.

FIG. 5 illustrates another preferred embodiment of the evaporation controller. As shown, the inner tube 30 does not have oppositely aligned racks and a sheet of absorbent paper is fitted on the inner surface of the inner tube 30.

When in use, first press the spray nozzle 21 of the inner container 2 to spray deodorizer into the inner tube 30. Then, the liquid deodorizer is retained by the absorbent paper 6. Thereafter, insert a coin (not shown) or the like in the groove 51 of the inner tube 30 and turn the inner tube 30 to adjust the passage going through the inner tube 30 and the outer tube 40 thereby controlling the evaporation rate of the deodorizer.

Figure 6:
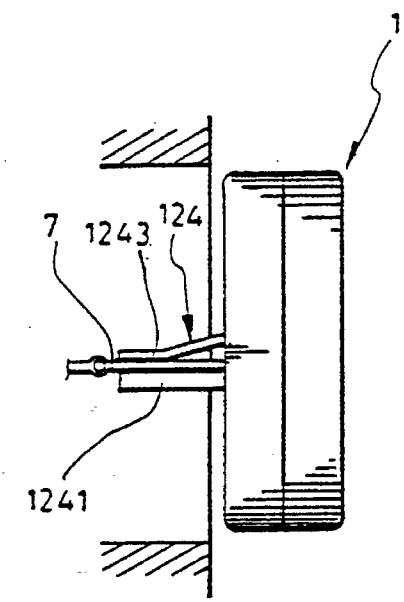
FIG. 6 illustrates how the deodorizer container is mounted on a horizontal louver of an air conditioner.

FIG. 6 illustrates how the deodorizer container is mounted on a horizontal louver of an air conditioner. As illustrated, the holder 124 is fitted on a horizontal louver 7 of an air-conditioner (not shown) so that the horizontal louver 7 is tightly clamped between the supporting members 1241 and the positioning members 1243 of the holder 24 thereby keeping the deodorizer container in a firm position.

Figure 7:
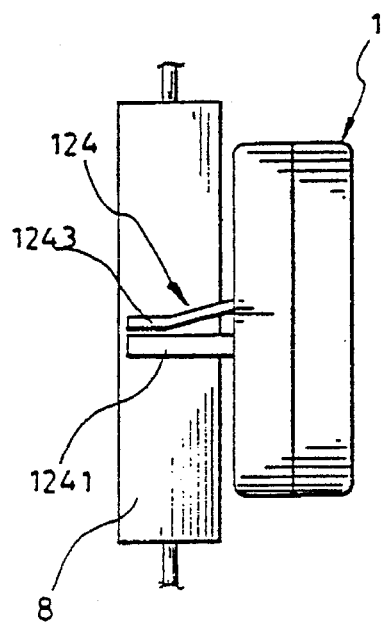
FIG. 7 illustrates how the deodorizer container is mounted on a vertical louver of an air conditioner.

FIG. 7 illustrates how the deodorizer is mounted on a vertical louver of an air conditioner. As shown, the holder 124 is fitted on a vertical louver 8 of an air-conditioner so that the vertical louver 8 is tightly fitted between the gaps 1242 of the supporting members 1241 and the positioning members 1243 hence conveniently mounting the deodorizer container thereon.

The invention is naturally not limited in any sense to the particular features specified in the forgoing or to the details of the particular embodiment which has been chosen in order to illustrate the invention. Consideration can be given to all kinds of variants of the particular embodiment which has been described by way of example and of its constituent elements without thereby departing from the scope of the invention. This invention accordingly includes all the means constituting technical equivalents of the means described as well as their combinations.

I claim:

1. A deodorizer container comprising:

a casing;

an inner container fitted into said casing and designed for receiving liquid deodorizer, said inner container being provided with a spray nozzle at a top thereof; and an evaporation controller including an outer tube and an inner tube rotatably fitted into the outer tube, said outer tube being formed with a plurality of perforations, said outer tube being provided at an end with a cylindrical portion communicated with said outer tube through a slot, said cylindrical portion being adapted to receive the spray nozzle of said inner container, said inner tube being formed with a plurality of perforations aligned with the perforations of said outer tube.

2. The deodorizer container as claimed in claim 1, wherein said outer tube is formed with a circular groove at an inner surface close to another end and two opposite longitudinal notches extending from an outermost edge of the another end to said circular groove, said inner tube being open at a first end and provided close to a second end with two opposite protuberances adapted to slide into said circular groove through said notches.

3. The deodorizer container as claimed in claim 1, wherein said inner tube has a circular plate at the second end on which there is an elongated groove.

4. The deodorizer container as claimed in claim 1, wherein said housing is formed with a plurality of slots.

5. The deodorizer container as claimed in claim 1, wherein said housing is provided with a holder including a pair of supporting members and a pair of positioning members above the supporting members.

6. The deodorizer container as claimed in claim 1, wherein said inner tube is provided with two pairs of oppositely aligned racks adapted to receive two sheets of absorbent paper.

* * * * *